(12) United States Patent
Mioskowski et al.

(10) Patent No.: US 7,326,805 B2
(45) Date of Patent: Feb. 5, 2008

(54) METHOD FOR THE SYNTHESIS OF 4-HYDROXYISOLEUCINE AND THE DERIVATIVES THEREOF

(76) Inventors: Charles Mioskowski, 1, rue Baudelaire, Strasbourg (FR) F-67200; Cédric Catala, 43, Route de l'Hôpital, Appt 63, Strasbourg (FR) F-67100; Alain Wagner, 25, Quai des Bateliers, Strasbourg (FR) F-67000

( * ) Notice: Subject to any disclaimer, the term of this patent is extended or adjusted under 35 U.S.C. 154(b) by 0 days.

(21) Appl. No.: 10/555,875

(22) PCT Filed: May 7, 2004

(86) PCT No.: PCT/FR2004/001128

§ 371 (c)(1),
(2), (4) Date: Oct. 19, 2006

(87) PCT Pub. No.: WO2004/099120

PCT Pub. Date: Nov. 18, 2004

(65) Prior Publication Data

US 2007/0043240 A1  Feb. 22, 2007

(30) Foreign Application Priority Data

May 7, 2003 (FR) .................................. 03 05568

(51) Int. Cl.
*C07C 229/00* (2006.01)
(52) U.S. Cl. .................................................. 560/170
(58) Field of Classification Search ..................... None
See application file for complete search history.

(56) References Cited

FOREIGN PATENT DOCUMENTS

EP   0 623 580 A1   11/1994
WO   01/72688 A2   10/2001

OTHER PUBLICATIONS

Jackson et al, Journal of the Chemical Society, Perkins Transactions 1, Reduction of a-Amino Acids as a Route to 4-Hydroxylated a-Amino Acids. Concise Approaches to the Synthesis of Clavalanine, Erythro-4-Hydroxyornithine and (+)-Bulgecinine, 1994, (13), pp. 1719-1726.*

International Search Report of PCT/FR2004/001128, mailed Nov. 3, 2004.

Broca et al., "4-Hydroxyisoleucine: Effects of Synthetic and Natural Analogues on Insulin Secretion", European Journal of Pharmacology, vol. 390, No. 3, Mar. 2000, pp. 339-345, XP000908995.

Inghardt et al., "Organoaluminium Induced Ring-Opening of Epoxypyranosides IV. Synthesis and Structure of Gamma-Hydroxy-Isoleucine Stereoisomers and Their Corresponding Lactones", Tetrahedron, vol. 47, No. 32, Aug. 5, 1991, pp. 6469-6482, XP000611434.

Chemical Abstracts, vol. 85, No. 9, 1976, abstract No. 63319m, Hasan Mashooda et al., "The four diastereomeric lactones of gamma-hydroxyisoleucine", p. 592, col. 2, XP002266040.

* cited by examiner

*Primary Examiner*—Paul A. Zucker
(74) *Attorney, Agent, or Firm*—Nixon & Vanderhye P.C.

(57) ABSTRACT

The invention relates to a method for the synthesis of two isomers, at function OH, alone or in mixtures, of amino acids α or the derivatives thereof, having general formula (B), wherein: linkage C—O of the 4-position carbon (represented by symbol) denotes one or other of isomers III or IV, or mixtures thereof. Moreover, $R_1$ and $R_2$ represent: a hydrogen atom; or either $R_1$ or $R_2$ represents a hydrogen atom and the other substituent is a radical $R_a$, an acyl group —$COR_a$, such as acetyl, or a functional group —$COOR_a$, —$SO_2R_a$, —N ($R_a$, $R_b$), $R_a$ and $R_b$, which are identical or different, representing a C1-C12 linear or branched alkyl radical, optionally substituted, an aryl group with one or more aromatic rings and heterocycles, comprising between 5 and 8C, optionally substituted, or aralkyl, the alkyl substituent and the aryl group being as defined above; or $R_1$ and $R_2$ both represent a substituent as defined above. $R_3$ represents a hydrogen atom or $R_a$ and $R_4$ has the significance of $R_a$. The invention is characterised in that it comprises: the isomerisation of a compound having formula (I), wherein $R_1$, $R_2$, $R_a$, $R_3$ and $R_4$ are as defined above, such as to produce a compound having formula (II); and the reduction of the carbonyl function thereof which, depending on the catalytic system employed and the formula (I) compound used, produces one of the isomers having general formula (III) or (IV) or a mixture thereof having formula (B). The invention can be used for the synthesis of (2S, 3R, 4S)-4-hydroxyisoleucine.

20 Claims, 1 Drawing Sheet

METHOD FOR THE SYNTHESIS OF 4-HYDROXYISOLEUCINE AND THE DERIVATIVES THEREOF

This application is the US national phase of international application PCT/FR2004/001128, filed 7 May 2004, which designated the U.S. and claims priority of FR 03/05568, dated 7 May 2003, the entire contents of each of which are hereby incorporated by reference.

The invention relates to a process for preparing 4-hydroxyisoleucine and its derivatives, with this term covering the analogs which can be obtained by the process of the invention. The invention is directed, in particular, to preparing (2S, 3R 4S)-4-hydroxyisoleucine (4-OH-iLeu for short) and its derivatives.

4-OH-iLeu is a natural product which is isolated from fenugreek seed and which corresponds to the formula A:

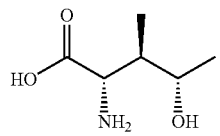

A

While this product is active, in particular, against type II diabetes, the quantities which can be obtained by extraction are insufficient to meet the needs of the population which is affected by this type of diabetes.

However, any interest in obtaining it synthetically comes up against the cost involved in doing this.

The inventors' research has related specifically to developing a process which comprises a reduced number of steps with this thereby making it utilizable on an industrial scale.

The invention is therefore directed towards a process for synthesizing, alone or in mixtures, the two isomers, at the OH function, of the α amino acids, or their derivatives, of the general formula B:

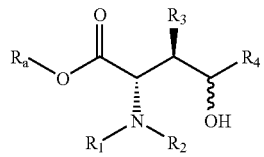

B in which
the C—O bond of the carbon in position 4 symbolizes one or other of the III or IV isomers, or their mixtures,
$R_1$ and $R_2$ represent:
a hydrogen atom, or
either $R_1$ or $R_2$ represents a hydrogen atom and the other substituent is a radical $R_a$, an acyl group —$COR_a$, in particular acetyl, or else a functional group —$COOR_a$, —$SO_2R_a$ or —N($R_a,R_b$), with $R_a$ and $R_b$, which are identical or different, being a linear or branched C1-C12 alkyl radical, which is optionally substituted, an aryl group having one or more aromatic and heterocycle rings comprising 5 to 8C, which is optionally substituted, or aralkyl, with the alkyl substituent and the aryl group being as defined above, or $R_1$ and $R_2$ both represent a substituent as defined above,
$R_3$ represents a hydrogen atom or $R_a$, and
$R_4$ has the meanings of $R_a$, characterized in that it comprises:
the isomerization of a compound of the formula I:

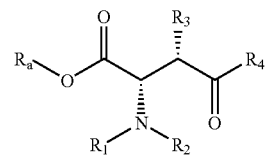

I in which $R_1$, $R_2$, $R_a$, $R_3$ and $R_4$ are as defined above, so as to obtain a compound of the formula II:

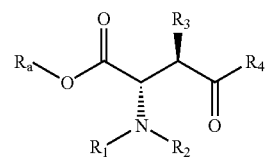

II the reduction of its carbonyl function, which leads, depending on the catalytic system which is used and the compound of the formula I which is employed, to one of the isomers of the general formula III or VI:

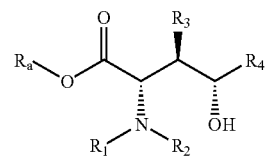

III

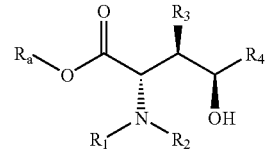

IV or to their mixture of the formula B
with the substituents $R_a$ and $R_1$ to $R_4$ being as defined above.

The transformation of the diastereoisomer I into the diastereoisomer II, with both being enantiomerically pure, is a dynamic isomerization which makes it possible, by the specific crystallization of the compound II, to completely displace the equilibrium from I to II and to isolate the pure compound II if desired.

In one embodiment of the invention, the synthetic process is characterized in that the isomerization step is followed by a step of total or partial deprotection of the amine function, leading to the formation of the compound XXIII

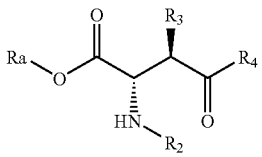

XXIII and then by a step of reduction of the carbonyl function, so as to lead to, as the main or sole compound, the lactone of the formula VII

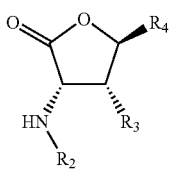

VII the opening of which leads predominantly to the compound of the formula C

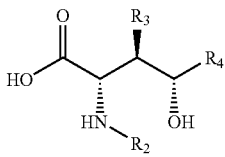

C

The compound C is purified by recrystallization, if necessary.

In another embodiment of the invention, the synthetic process is characterized in that the isomer III obtained by isomerization of the compound I and reduction of the compound II undergoes hydrolysis of its ester function in order to lead to the compound of the formula V:

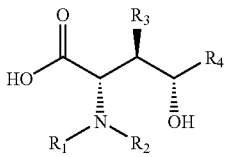

V at least one of whose groups protecting the nitrogen function is eliminated, if desired, in order to lead to the compound of the general formula C:

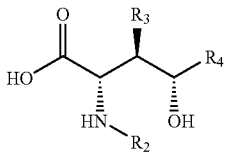

C

In another embodiment, the protective group R1 of III can be eliminated using standard methods, with this leading to the compound of the formula VI:

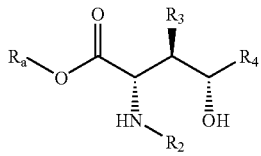

VI whose ester function is hydrolyzed in order to lead to the compound C.

As a variant, the compound of the formula VI is cyclized to form a lactone of the formula VII:

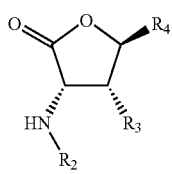

VII the opening of which then leads to the compound of the formula C above.

The isomer of the formula IV can be subjected to the same sequences, leading to a product of the general formula D:

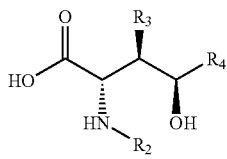

D

In yet another embodiment of the invention, the isomer II or the isomer III leads, by cyclization, to a lactone of the formula VIII or IX:

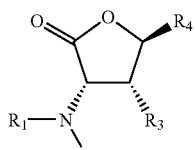

VIII

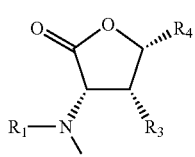

IX which can be separated, for example by means of chromatography or crystallization.

The lactone VIII can be converted into the lactone VII by total or partial deprotection of the amine function and the lactone IX cana be converted into a lactone X:

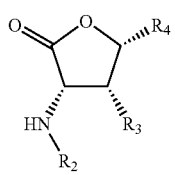

X

The lactones VII and X are then hydrolyzed in order to lead to the compounds of the general formulae C and, respectively, D above.

The isomerization step is carried out, with or without solvent, in the presence of a base, by creating conditions for precipitating the compound II, with this displacing the equilibrium towards this compound.

Appropriate solvents include ethanol, benzene, toluene and, preferably, aprotic solvents such as hexane, tetrahydrofuran or tert-butyl methyl ether.

The base is, for example, a phosphazene or an amino base such as triethylamine, DBN (1,4-diaza-bicyclo[4.3.0]non-5-ene) or DBU (1,8-diaza-bicyclo[5.4.0])undec-7-ene).

It is also possible to use organometallic systems, bases supported on polymers, for example amines grafted onto polystyrene, supported ammonium hydroxides or aluminosilicates, or, as a variant, an alkaline metal salt such as potash or potassium carbonate.

After the precipitated compound II has been filtered off, the isomer II is recrystallized in an appropriate solvent such as methanol, hexane or, preferably, ethanol, at temperatures ranging from −60° C. to 30° C.

As pointed out above, the isomer II can be subjected to a step of total or partial deprotection of the amine function. This deprotection is carried out in a conventional manner. When $R_1$ represents an oxidizable protective group, such as p-methoxyphenyl, recourse is had, for example, to cerium and ammonium nitrate or to the electrochemical route, or use is made, as reagents, of (ammonium, sodium, potassium, etc.) persulfates, perborates, manganese dioxide, potassium permanganate, $H_2O_2$, $FeCl_3$ or a combination of cerium compound and an oxidizing agent.

This step is not followed by any purification, and a simple extraction makes it possible to move on to the reduction, in aqueous medium, of the carbonyl function, for example using potassium borohydride in aqueous medium accompanied by $CeCl_3$ in catalytic quantity. This step leads to the mixture of the two possible diastereoisomers, with the compound VII which is described in the literature being in the majority, passing by way of the open intermediate (not isolated) of the formula VI.

As a variant, the isomer II which is recovered at the end of the isomerization step is subjected to a step of reduction of the carbonyl function.

The formation of one of the compounds III, IV, VIII and IX can be favored in dependence on the operational conditions which are employed.

The reduction is effected, for example, in a solvent of the ethanol type, to which a reduction catalyst, if necessary a reactivity modifier and the isomer II, are added, after which the mixture is purged with hydrogen. The reaction mixture is then stirred under a hydrogen pressure ranging from 1 bar to 50 bars and at ambient temperature.

In order to favor the formation of the compounds III and IV, the reduction is carried out under a hydrogen pressure of the order of 50 bars.

In order to favor the formation of the compounds VIII and IX, the reduction is carried out under a hydrogen pressure of the order of atmospheric pressure.

An example of the invention consists in favoring the predominant isolation of one of the two diastereoisomers VIII and IX by varying the nature of the catalyst and of the additive employed.

In particular, the reduction, under 1 atmosphere, of II in the presence of ruthenium black preferentially leads to the formation of the compound IX and the reduction of II in the presence of Raney nickel preferentially leads to the formation of the compound VIII.

An example of an additive which is employed is DABCO (1,4-diazobicyclo[2.2.2]octane) which reverses the selectivity of the Raney nickel.

Thus, a reduction which is effected, for example, under 1 atmosphere of hydrogen and in a solvent of the ethanol type to which Raney nickel, which is suspended in the ethanol, DABCO and the isomer II are added preferentially leads to the formation of the compound IX.

Whatever the sequence, the ester function of the products III and IV is hydrolyzed by treating in alkaline medium, advantageously with LiOH, or in an aqueous alcoholic solvent using methods which are known per se.

The lactones of the formulae VIII and IX are also hydrolyzed, for example, by using LiOH in THF.

Whatever the sequence, the $R_1$ grouping is advantageously eliminated using standard methods; for example, the para-methoxyphenyl group is eliminated by treating with cerium and ammonium nitrate (CAN) or by the electrochemical route.

In accordance with the invention, the compound of the formula I is advantageously obtained by condensing a ketone of the formula XI:

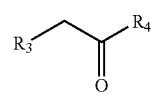

XI with an imine of the formula XII:

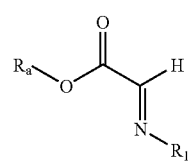

XII in the presence of a chiral catalyst of the general formula XIII, which can be of the R or S configuration at the carbon in position 2:

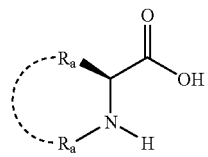

XIII

The two substituents $R_a$, which are identical or different, are as defined above and can additionally form a ring, in particular having 5 to 8 members.

Other enantiospecific condensation catalysts can also be used.

The condensation step is advantageously effected in a polar or ionic solvent and in the presence of a recyclable catalyst. Depending on the stereochemistry of the catalyst, one or other of the compounds of the general formula I, or its mirror image XIV:

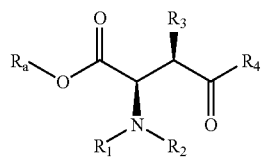

XIV is obtained. The compound XIV can undergo the same steps as the compound of the formula I.

After the condensation, $R_2$ in the compound of the formula I represents a hydrogen atom. A grouping $R_2$, which is different from hydrogen, can be introduced using standard methods, if desired. Thus, in order to introduce an alkyl, carbamyl, sulfonyl or acyl, in particular acetyl, substituent, use is made, for example, of an appropriate alkylating, carbamoylating, sulfonylating or acylating agent, advantageously of acetic anhydride for the purpose of synthesizing the acetylated derivatives.

Appropriate solvents include dimethyl sulfoxide (DMSO), ethanol (EtOH), or else dimethylformamide (DMF). Particularly satisfactory catalysts include L-proline or the derivatives of trans-hydroxy proline.

The imines of the formula XII are advantageously obtained by condensing a glyoxalate XV

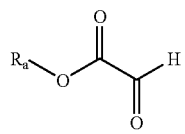

XV with an amine $R_1NH_2$.

The invention is very specifically directed towards obtaining 4-hydroxyisoleucine of the formula A above, in accordance with a process which comprises:

the condensation of the compound of the formula XVI

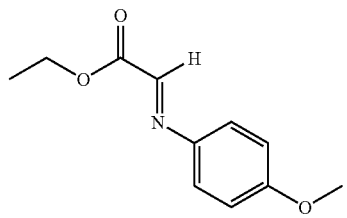

XVI with 2-butanone, in the presence of L-proline, with this predominantly leading to the compound of the formula XVII,

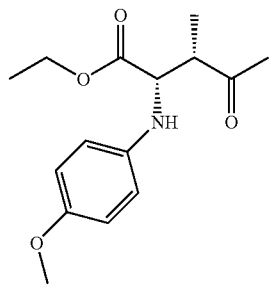

XVII followed by its isomerization/crystallization by treatment of XVII with DBU or DBN, with this leading to the compound XVIII:

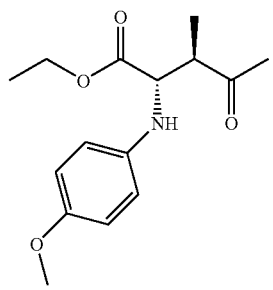

XVIII elimination of the para-methoxyphenyl protective group by treatment with a persulfate, reduction of the deprotected compound with $KBH_4/CeCl_3$ in ethanol or water, with this leading to the lactone XX:

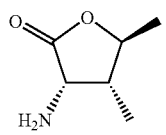

XX which, by means of hydrolysis in LiOH/THF, predominantly leads to the compound A. This compound is isolated and crystallized.

In another mode of synthesizing 4-hydroxyisoleucine, the compound XVIII is reduced before being deprotected.

As novel products, the invention is also directed towards the intermediate compounds in the above-described operational steps.

Thus, the invention is directed, in particular, towards the compounds corresponding to the general formula II. A more specifically preferred product corresponds to the compound XVIII.

The invention is also directed towards the intermediate compounds of the general formula XXIII. A particularly preferred compound which meets this formula corresponds to the compound XXIV.

The invention is yet again directed towards the intermediate products of the general formula VIII as such. It is especially directed towards the product XIX.

Examples of implementing the abovementioned steps are described below for the purpose of illustrating the invention. A general scheme of the reactions which can be brought into play is given in the sole figure.

EXAMPLE I

Obtaining the Imines

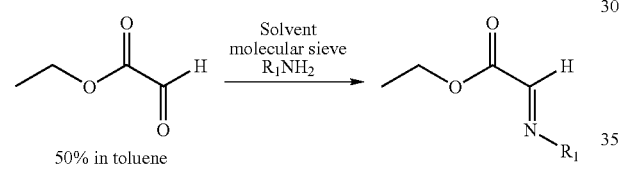

Figure 1:
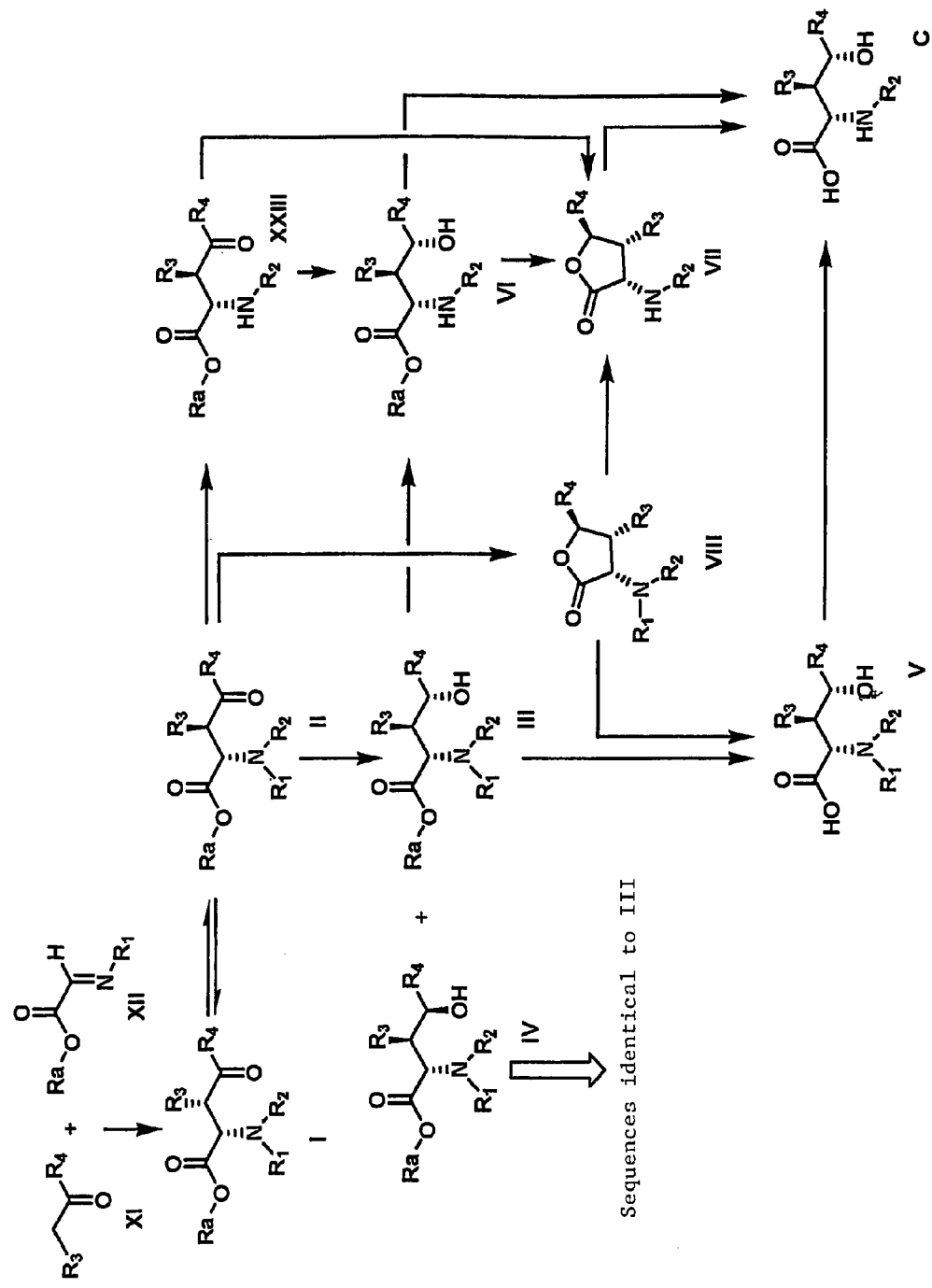
FIG. 1 provides a general scheme of the reactions which can be brought into play in the present invention.

General Method of Operation 1 g of ethyl glyoxalate (V=2 ml) is added, in 20 ml of anhydrous solvent (toluene or dichloromethane depending on the stability of the imine which is formed), to a two-necked round-bottomed flask which has been flamed under argon and which contains 6 g of molecular sieve. After that, 1 equivalent of amine is added and the mixture is stirred vigorously at ambient temperature for 2 hours.

The crude reaction product is filtered through Celite® and then evaporated under reduced pressure. It is used as it is, without purification, in the following condensation step.

| Entry | Imine formed | Yield |
|---|---|---|
| 1 | (structure with N-OH) | 90% |
| 2 | (structure with N-OMe) | 40% |
| 3 | (structure with N-O-acetyl) | 70% |
| 4 | (structure with N-phenyl) | 95% |
| 5 | (structure with N-C6H4-OMe) | 98% |
| 6 | (structure with N-CH2-phenyl) | 86% |
| 7 | (structure with N-CH2-C6H4-OMe) | 95% |
| 8 | (structure with N-CH(CH3)-phenyl) | 97% |

-continued
| Entry | Imine formed | Yield |
|---|---|---|
| 10 | 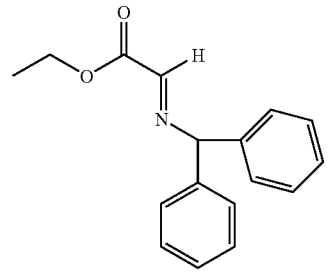 | 95% |
| 11 | 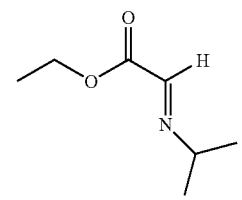 | 90% |
| 12 | 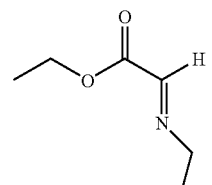 | 98% |
-continued
| Entry | Imine formed | Yield |
|---|---|---|
| 13 | | 55% |
| 14 | | 80% |
EXAMPLE II
Obtaining a Mixture of Isomers E, F and G in Accordance with the Following Scheme
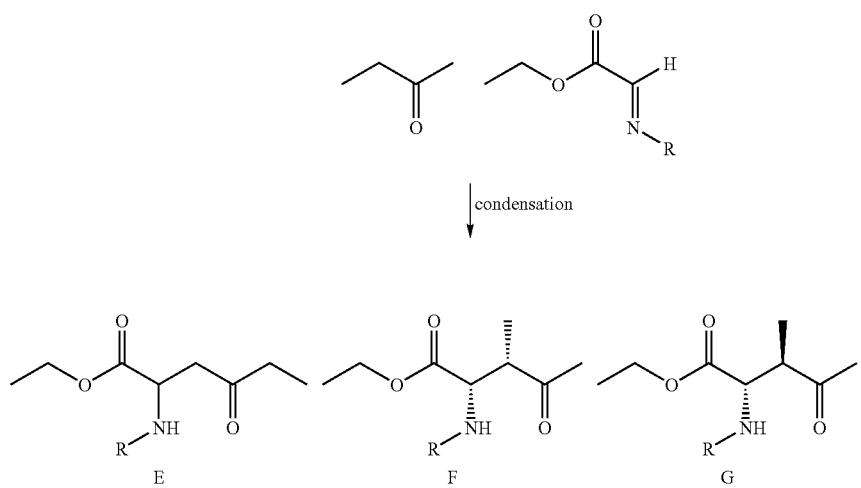

in which R=-PMP (para-methoxyphenyl)

Method of Operation A 2.8 ml of solvent, 2 ml of butanone and 0.35 equiv. of L-proline are placed in a two-necked round-bottomed flask, after which the imine (1 mmol) is added. The reaction medium is stirred for 2 h and then diluted in 10 ml of ethyl acetate and 10 ml of phosphate buffer solution, pH=7.4. The organic phase is recovered, dried over MgSO$_4$ and then filtered through Celite®. The crude reaction product is evaporated and chromatographed through a silica column.

The operational conditions and the results obtained are summarized in Table 1 below.

TABLE 1

| Exp. No. | Solvent (conc.) | Catalyst | Reaction time | Yield (F) | Enantiomeric excess (F) | G/F/E ratio |
|---|---|---|---|---|---|---|
| 1 | DMSO (0.125 M) | L proline | 2 h 15 | 75% | 99/1 | 0/90/10 |
| 2 | DMSO (0.125 M) | L Proline | 2 h 53 | 71% | 100/0 | 0/88/12 |
| 3 | DMSO (0.4 M) | L proline | 3 h 34 | 71% | 100/0 | 0/88/12 |
| 4 | DMSO (0.125 M) | DL proline | 2 h 05 | 73% | 50/50 | 0/88/12 |
| 5 | DMSO (0.125 M) | T hydroxyproline | 23 h 30 | 73% | 100/0 | 0/88/12 |
| 6 | EtOH (0.125 M) | L proline | 3 h 00 | 70% | 96/4 | 0/91/8 |
| 7 | DMF (0.125 M) | L proline | 3 h 45 | 73% | 100/0 | 0/90/10 |
| 8 | [methylimidazolium butyl Br] (0.125 M) | L proline | 3 h 30 | 61% | 100/0 | 0/96/4 |
| 9 | [methylimidazolium butyl Br] (0.4 M) | L proline | 1 h 20 | 61% | — | 0/95/5 |
| 10 | [methylimidazolium butyl Br] (one pot 0.2 M) | L proline | 19 h 00 | 53% | | 0/91/8 |
| 11 | [methylimidazolium butyl Br] (0.2 M) 70° C. | T hydroxyproline | 1 h 20 | 44% | — | 0/95/5 |

OTHER CONDENSATION EXAMPLES

TABLE 2

| Product | G/F/E | GC yield |
|---|---|---|
| (benzyl-NH, ethyl ester, methyl ketone) | 70/30/0 | 62% |
| (p-methoxybenzyl-NH, ethyl ester, methyl ketone) | 60/40/0 | 50% |
| (allyl-NH, ethyl ester, methyl ketone) | 70/30/0 | 77% |
| (isopropyl-NH, ethyl ester, methyl ketone) | 70/30/0 | 46% |
| (1-phenylethyl-NH, ethyl ester, methyl ketone) | Exception because 4 dias. in the same proportions | 20% |

TABLE 2-continued

| Product | G/F/E | GC yield |
|---|---|---|
| (ethyl ester with NH-C6H4-OMe, methyl ketone) | 0/95/5 | 88% |
| (ethyl ester with NH-C6H5, methyl ketone) | 0/88/12 | 78% |
| (ethyl ester with NH-tosyl, methyl ketone) | 10/70/20 | 65% |

EXAMPLE III

Isomerization of the F Isomer

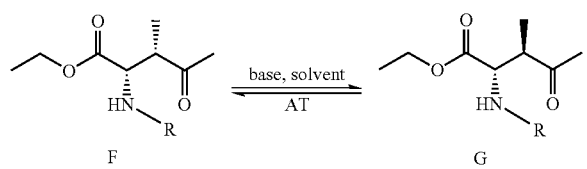

TABLE 3

| | R = –PMP | | |
|---|---|---|---|
| Solvent | Base | F | G |
| EtOH | Et₃N | 40 | 60 |
| Toluene | DBN | 40 | 60 |
| TBME | DBN | 40 | 60 |
| None | DBN | 20 | 80 |
| TBME (method by evaporation) | DBN | 5 | 95 |

Method of Operation B

EXAMPLE IV

Reduction of the Carbonyl Function and Lactonization

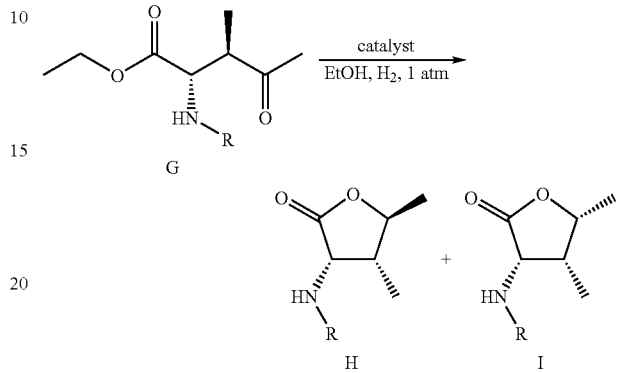

The results obtained are given in Table 4.

TABLE 4

| | (R = –PMP) | |
|---|---|---|
| Catalyst | H | I |
| NiR/H₂O | 60 | 40 |
| NiR/DABCO | 30 | 70 |
| NiR/B(iPrO)₃ | 70 | 30 |
| Ni sponge | 50 | 50 |
| Ru black | 25 | 75 |

Method of Operation.

The ethanol (1 ml), the solution of Raney nickel in ethanol (100 μl) and G (20 mg, 1 equiv., 0.71.10$^{-4}$ mol) are introduced into a 5 ml single-necked round-bottomed flask. The whole is brought to 0° C. and then purged with hydrogen.

The medium is stirred under hydrogen pressure (1 atm.) at ambient temperature for 24 hours.

The crude reaction product is purified by chromatography on a silica column and the compounds H and I are isolated with a yield of 90%. The proportions of each diastereoisomer are specified by $^1$H NMR.

Reduction of the carbonyl function without lactonization

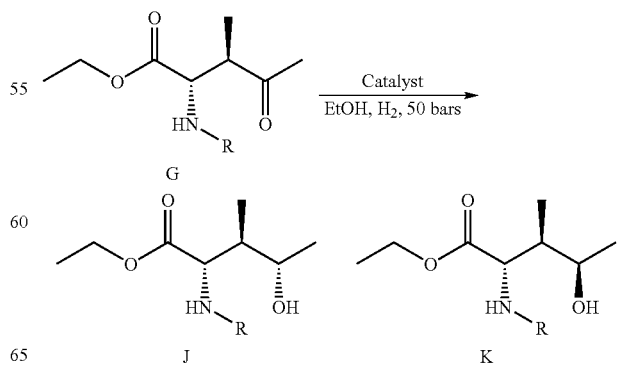

TABLE 5

| Catalyst | J | K |
|---|---|---|
| NiR | 60 | 40 |
| Pt/C | 60 | 40 |

Method of Operation.

The ethanol (3 ml), the solution of Raney nickel in ethanol (300 µl) and G (60 mg, 1 equiv., $2.1.10^{-3}$ mol) are introduced into a 100 ml autoclave. The whole is purged three times with hydrogen.

The medium is stirred under a hydrogen pressure of 50 bars at ambient temperature for 24 hours.

The crude reaction product is purified by chromatography on a silica column and compounds J and K are isolated with a yield of greater than 90%. The proportions of each diastereoisomer are specified by $^1$H NMR.

EXAMPLE V

Elimination of the $R_1$ Grouping—in Accordance with the Following Scheme

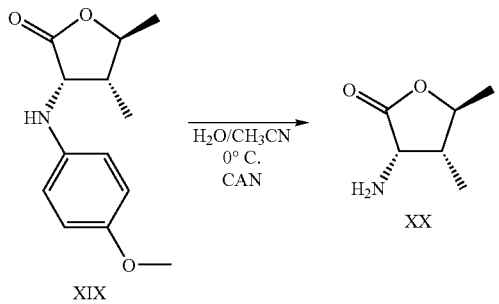

Method of Operation:

- the starting lactone (1 mmol) in $CH_3CN$ (4.9 ml) is placed, at 0° C., in a two-necked round-bottomed flask and CAN (30 g) in 1 ml of water is added. The mixture is left to stir for 40 min after which 10 ml of water together with 20 ml of dichloromethane are added. The aqueous phase is extracted three times with 10 ml of dichloromethane and then alkalinized to a pH of 9 by adding sodium carbonate.
- the alkaline aqueous phase is then extracted seven times with dichloromethane. The organic phases are pooled and dried over $MgSO_4$, after which they are evaporated.
- the desired product is obtained with a yield of 38%.

As a variant, the deprotection is effected by the electrochemical route using a platinum working electrode, a platinum counterelectrode and an Ag/AgCl reference electrode. The electrolysis is carried out at 0.7 V for 5 h. The treatment is identical to that of the standard method. The desired lactone is obtained with a yield of 21%.

The same methods are applied for obtaining the compound XXII from the compound XXI.

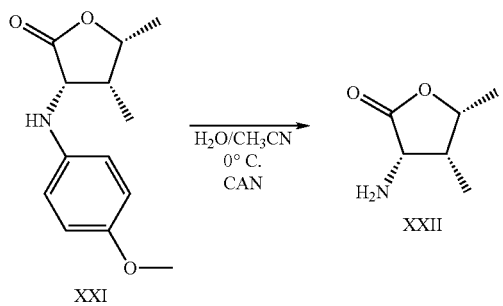

Hydrolysis and Purification

The mixture of lactones (90/10) is dissolved in 96 ml of water (0.3M) and lithium hydroxide (1.1 g, 43.3 mmol, 1.5 equiv.) is added at ambient temperature. After two hours of stirring, the reaction medium is acidified with acetic acid (43.3 mmol, 2.4 ml) and the whole is then brought under vacuum in order to eliminate any trace of water, solvent or acid.

The gum which is obtained is dissolved in ethanol and 1.56 g of the pure (2S, 3R, 4S)-4-hydroxyisoleucine are recrystallized selectively (80% yield).

Analyses

The GC/MS analyses are all carried out on the same type of material.

GC/MS (Shimadzu GCMS-QP5050A)

SGE CAPILLARY silica column, 25 m×0.22 mm, BPX5 0.25

Program

Interface: 260° C.

Column: 80° C.

Detector: 320° C.

2 min at 80° C. then temperature increase by 10° C./min

The HPLC analyses are all carried out on the same type of material.

HPLC (Gynkotek Gina 50) and ZORBAX SIL column 4.6 MM ID×25 cm

Eluent: Hexane/ethanol, 95/05

Flow rate: 6 ml/min

Compound XX

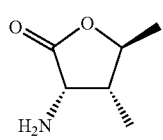

$^1$H NMR (CDCl$_3$, 200 MHz) δ (ppm): 1.10 (d), 1.40 (d), 1.82 (s), 2.30 (m), 3.80 (d), 4.32 (m) MS(IC) m/z: [M+H]$^+$=130 GC/MS $t_R$=6.22 min Compound XXII

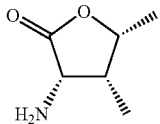

XXII

¹H NMR (CDCl₃, 300 MHz) δ (ppm): 0.91 (d), 1.36 (d), 1.82 (s), 2.59 (m), 3.85 (d), 4.53 (m) MS(IC) m/z: [M+H]⁺=130 GC/MS $t_R$=6.69 min Compound XIX

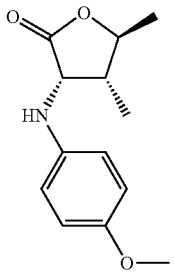

XIX

¹H NMR (CDCl₃, 300 MHz) δ (ppm): 0.99 (d), 1.48 (d), 2.65 (m), 3.74 (s), 3.98 (s), 4.24 (m), 4.40 (q), 6.71 (2*d) ¹³C NMR (CDCl₃, 75 MHz) δ (ppm): 13.36; 20.31; 40.25; 55.60; 55.95; 81.82; 114.15; 114.85; 128.21; 140.75; 152.72; 175.78 MS(IC) m/z: [M+H]⁺=236 HPLC $t_R$=5.053 min Compound XXI

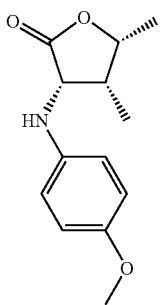

XXI

¹H NMR (CDCl₃, 300 MHz) δ (ppm): 0.82 (d), 1.39 (d), 2.89 (m), 3.74 (s), 4.13 (s), 4.19 (m), 4.68 (m), 6.71 (2*d) ¹³C NMR (CDCl₃, 75 MHz) δ (ppm): 6.9; 15.31; 39.33; 55.60; 59.39; 76.86; 113.99; 114.88; 140.58; 152.65; 175.84 MS(IC) m/z: [M+H]⁺=236 HPLC $t_R$=5.382 min Compound XVII

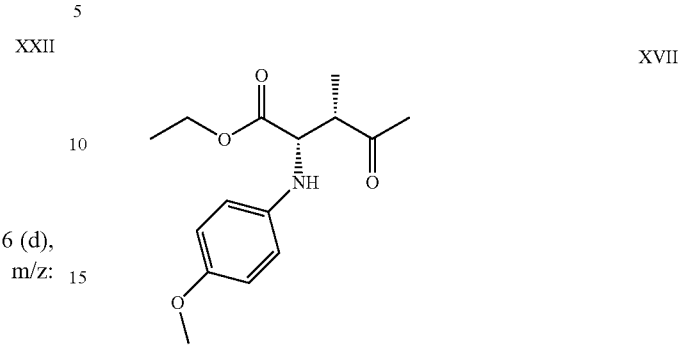

XVII

¹H NMR (CDCl₃, 200 MHz) δ (ppm): 1.21 (t), 1.23 (d), 2.21 (s), 3.01 (m), 3.72 (s), 3.90 (s), 4.15 (q), 4.35 (d), 6.70 (2*d) ¹³C NMR (CDCl₃, 200 MHz) δ (ppm): 209.58; 173.20; 153.50; 141.19; 116.18; 115.20; 61.72; 59.98; 56.05; 49.62; 28.89; 14.54; 12.64 MS(IC) m/z: [M+H]+=280 GC/MS $t_R$=17.33 min Compound XVIII

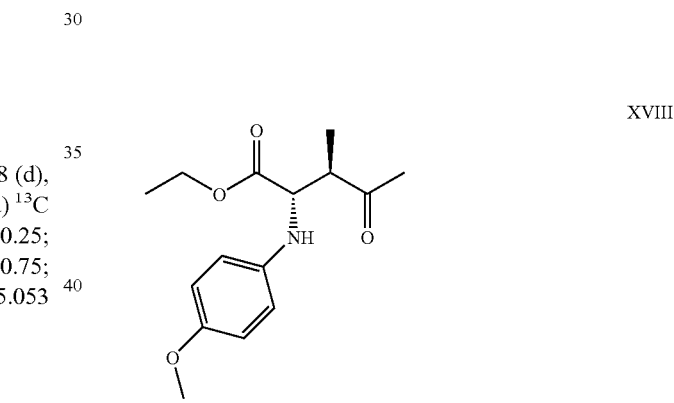

XVIII

Chirality
HPLC column: Chiralpak AS
Eluent: Hexane/EtOH, 90/10
Flow rate: 1 ml/min
UV: 220 nm
Temperature: 30° C.
Retention time: 6.67 min
$α_D$: −35.5 (CH₂Cl₂ C=1.0)
m.p.: 98.8-99.1° C.

¹H NMR (CDCl₃, 300 MHz) δ (ppm): 1.19 (d), 1.22 (t), 2.23 (s), 3.02 (m), 3.73 (s), 4.15 (q, d, s) 6.74 (2*d) ¹³C NMR (CDCl₃, 50 MHz) δ (ppm): 12.85; 14.00; 28.47; 49.19; 55.48; 60.30; 61.09; 114.67; 115.60; 140.60; 152.90; 172.38; 209.35 MS(IC) m/z: [M+H]⁺=280 GC/MS $t_R$=17.27 min IR: ν(NH)=3357 cm⁻¹ ν(CO)=1733 cm⁻¹ and 1715 cm⁻¹

Compound XVI

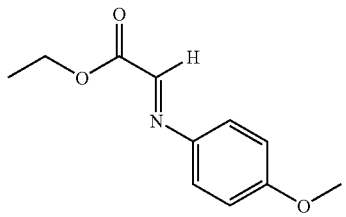

$^1$H NMR (CDCl$_3$, 300 MHz) δ (ppm): 1.38 (d), 3.82 (s), 4.39 (q), 6.91 (d), 7.35 (d), 7.92 (s) $^{13}$C NMR (CDCl$_3$, 75 MHz) δ (ppm): 14.13; 55.20; 59.81; 118.28; 122.01; 142.1; 143.61; 157; 165.23 MS(IC) m/z: [M+H]$^+$=208 GC/MS $t_R$=8.47 min (increase of 25° C./min)

Compound XXIV

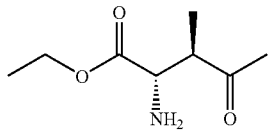

Gum
$^1$H NMR: (CDCl$_3$, 300 MHz) δ (ppm): 0.94 (d), 1.03 (t), 1.50 (s), 1.98 (s), 2.71 (m), 3.33 (d), 3.94 (m)
$^{13}$C NMR: (CDCl$_3$, 50 MHz) δ (ppm): 12.69; 13.50; 28.22; 49.78; 56.26; 60.30; 173.76; 209.45 α$_D$: -52.9 (CH$_2$Cl$_2$ C=1.0) MS(IC) m/z: [M+H$^+$]174 IR: ν(CO)=1734 cm$^{-1}$ and 1716 cm$^{-1}$

The invention claimed is:
1. A process for synthesizing, alone or in mixtures, the two isomers, at the OH function, of the α amino acids, or their derivatives, of the general formula B:

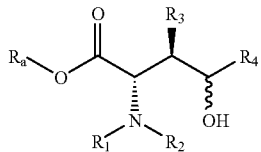

in which
the C—O bond of the carbon in position 4 symbolizes one or other of the III or IV isomers, or their mixtures,
R$_1$ and R$_2$ represent:
a hydrogen atom, or
either R$_1$ or R$_2$ represents a hydrogen atom and the other substituent is a radical R$_8$, an acyl group —COR$_a$, or else a functional group —COOR$_a$, —SO$_2$R$_a$ or —N(R$_a$,R$_b$), with R$_a$ and R$_b$, which are identical or different, being a linear or branched C1-C12 alkyl radical, which is optionally substituted, an aryl group having one or more aromatic and heterocycle rings comprising 5 to 8C, which is optionally substituted, or aralkyl, with the alkyl substituent and the awl group being as defined above, or R$_1$ and R$_2$ both represent a substituent as defined above,
R$_3$ represents a hydrogen atom or R$_a$, and
R$_4$ has the meanings of R$_a$,
chamcterized in that it comprises:
the isomerization of a compound of the formula I:

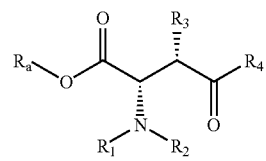

in which R$_1$, R$_2$, R$_9$, R$_3$ and R$_4$ are as defined above, so as to obtain a compound of the formula II:

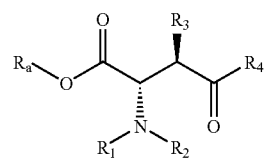

the reduction of its carbonyl function, which leads, depending on the catalytic system which is used and the compound of the formula I which is employed, to one of the isomers of the general formula III or VI or to their mixture of the formula B:

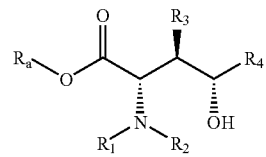

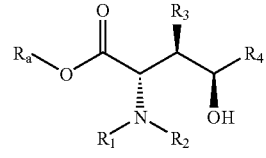

with the substituents R$_a$ and R$_1$ to R$_4$ being as defined above.
2. The process as claimed in claim 1, characterized in that the isomerization step is followed by a step of total or partial deprotection of the amine function and then by a step of reduction of the carbonyl function so as to lead to, as the major or sole compound, the lactone of the formula VII

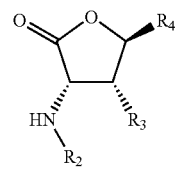

the opening of which leads to a mixture which mainly comprises the compound of the formula C

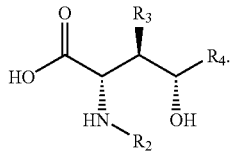

C

3. The process as claimed in claim 1, characterized in that the isomer III obtained by isomerization of the compound I and reduction of the compound II undergoes hydrolysis of its ester function in order to lead to the compound of the formula V;

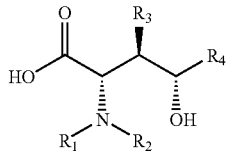

V at least one of whose groups protecting the nitrogen function is eliminated, if desired, in order to lead to the compound of the general formula C:

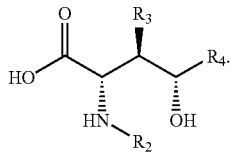

C

4. The process as claimed in claim 3, characterized in that the protective group R1 of the compound III is eliminated, with this leading to the compound of the formula VI:

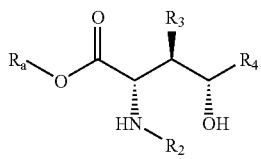

VI whose ester function is hydrolyzed in order to lead to the compound C.

5. The process as claimed in claim 3, characterized in that the compound of the formula VI is cyclized to form a lactone of the formula VII:

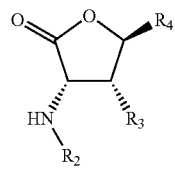

VII with the opening of this lactone then leading to the compound of the formula C, or in that the isomer II is reduced and then cyclized to form a compound of the formula VIII:

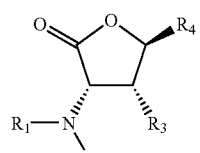

VIII which is deprotected to form the compound of the formula VII, then leading to the compound of the formula C.

6. The process as claimed in claim 1, characterized in that the isomer of the formula IV is subjected to the sequences as claimed in claim 2 or 3, with this leading to a product of the general formula D:

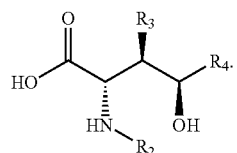

D

7. The process as claimed in claim 1, characterized in that the isomer II is reduced and cyclized so as to lead to a lactone of the formula VIII or IX:

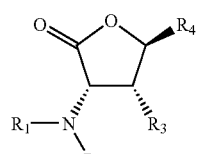

VIII

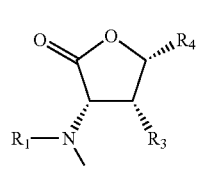

IX with it being possible to separate these lactones, for example by means of chromatography or crystallization.

8. The process as claimed in claim 6, characterized in that the lactone VIII is converted into a lactone VII by total or partial deprotection of the amine function and the lactone IX is converted into a lactone X:

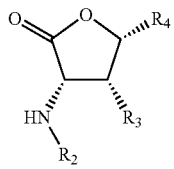

X with these lactones VII and X then being hydrolyzed in order to lead to the compounds of the general formulae C and, respectively, D as claimed in claim 2.

9. The process as claimed in claim 1, characterized in that the isomerization step is carried out with or without solvent, in the presence of a base, by creating conditions for precipitating the compound II, with this displacing the equilibrium towards this compound.

10. The process as claimed in claim 1, characterized in that the isomer II is subjected to a step of total or partial deprotection of the amine function, with this step being carried out such that when $R_1$ represents an oxidizable protective group, such as p-methoxyphenyl, recourse is had, for example, to cerium and ammonium nitrate or to the electrochemical route, or use is made, as reagents, of (ammonium, sodium, potassium, etc.) persulfates, perborates, manganese dioxide, potassium permanganate, $H_2O_2$, $FeCl_3$ or a combination of cerium compound and an oxidizing agent.

11. The process as claimed in claim 10, characterized in that the deprotected product of the formula XXIII is subjected to a step of reduction, in aqueous medium, of the carbonyl function, with this predominantly leading to the compound VII.

12. The process as claimed in claim 1, characterized in that the isomer II which is recovered at the end of the isomerization step is subjected to a step of reduction of the carbonyl function.

13. The process as claimed in claim 12, characterized in that the hydrolysis of the ester function of the products III and IV is effected by treating in alkaline medium, advantageously with LiOH, or in an aqueous alcoholic solvent.

14. The process as claimed in claim 4, characterized in that the lactones of the formulae VIII and IX are hydrolyzed using LiOH in THF.

15. The process as claimed in claim 1, characterized in that the compound of the formula I is obtained by condensing a ketone of the formula XI:

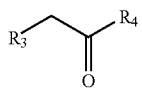

XI with an imine of the formula XII:

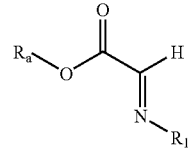

XII in the presence of a chiral catalyst of the general formula XIII, which can be of the R or S configuration at the carbon in position 2:

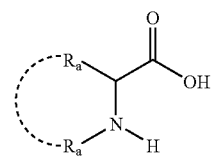

XIII and in which the two substituents $R_a$, which are identical or different, are as defined above and can additionally form a cycle, in particular of from 5 to 8 members.

16. The process as claimed in claim 15, characterized in that the condensation step is carried out in a polar or ionic solvent and in the presence of a recyclable catalyst, with this leading, depending of the stereochemistry of the catalyst, to one or other of the compounds of the general formula I or to its mirror image XIV:

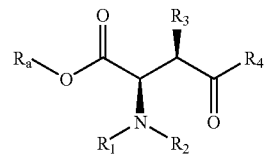

XIV with it being possible for the compound XIV to be subjected to the same steps as the compound of the formula I.

17. The process as claimed in claim 1, characterized by the introduction of a group $R_2$, which is different from a hydrogen atom, into the compound of the formula I.

18. The process as claimed in claim 15, characterized in that the imines of the formula XII are obtained by condensing a glyoxalate XV:

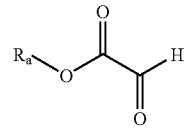

XV with an amine $R_1NH_2$.

19. A process for obtaining the 2S, 3R, 4S, 4-hydroxyisoleucine of the formula A as claimed in claim 1, characterized in that it comprises:
the condensation of 2-butanone with the Imine of the formula XVI:

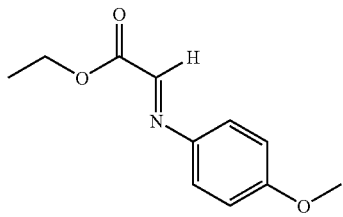

XVI in the presence of L-proline, which predominantly leads to the compound of the formula XVII:

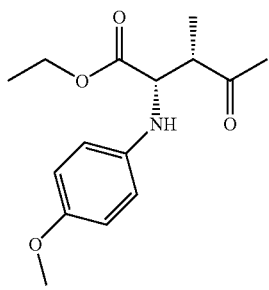

XVII followed by its isomerization/crystallization by means of treating XVII with DBU or DBN, which leads to the compound XVIII:

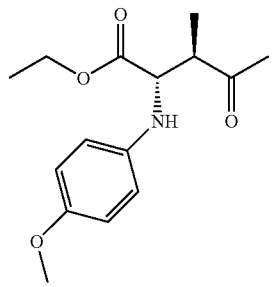

XVIII elimination of the p-methoxyphenyl protective group by treating with a persulfate, reduction of the deprotected compound with $KBH_4/CeCl_3$ in ethanol or water, which leads to the lactone XX:

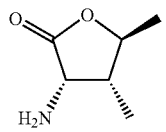

XX which, by means of hydrolysis in LIOH/THF, predominantly leads to the compound A.

20. The process of claim 1 wherein —$COR_a$ is acetyl.

* * * * *